(12) United States Patent
Enders

(10) Patent No.: US 10,352,885 B2
(45) Date of Patent: Jul. 16, 2019

(54) APPARATUS AND METHOD FOR PRODUCING AND ANALYZING A PLURALITY OF SAMPLE MATERIALS

(71) Applicants: ThyssenKrupp Industrial Solutions AG, Essen (DE); thyssenkrupp AG, Essen (DE)

(72) Inventor: Michael Enders, Münster (DE)

(73) Assignees: THYSSENKRUPP INDUSTRIAL SOLUTIONS AG, Essen (DE); THYSSENKRUPP AG, Essen (DE)

( * ) Notice: Subject to any disclaimer, the term of this patent is extended or adjusted under 35 U.S.C. 154(b) by 159 days.

(21) Appl. No.: 15/535,501

(22) PCT Filed: Dec. 15, 2015

(86) PCT No.: PCT/EP2015/079880
§ 371 (c)(1),
(2) Date: Jun. 13, 2017

(87) PCT Pub. No.: WO2016/096911
PCT Pub. Date: Jun. 23, 2016

(65) Prior Publication Data
US 2017/0363552 A1    Dec. 21, 2017

(30) Foreign Application Priority Data

Dec. 16, 2014    (DE) .......................... 10 2014 018 489

(51) Int. Cl.
*G01K 17/00*    (2006.01)
*G01K 1/00*    (2006.01)
(Continued)

(52) U.S. Cl.
CPC ......... *G01N 25/4853* (2013.01); *B02C 21/00* (2013.01); *B02C 25/00* (2013.01);
(Continued)

(58) Field of Classification Search
USPC .................................... 374/33, 31, 141, 208
See application file for complete search history.

(56) References Cited

U.S. PATENT DOCUMENTS 2,953,440 A    9/1960    Claudy

FOREIGN PATENT DOCUMENTS

DE    3517162 A    12/1985
DE    19634533 C    9/2001

OTHER PUBLICATIONS

English translation of International Search Report issued in PCT/EP2015/079880, dated Mar. 10, 2016 (Mar. 31, 2016).
(Continued)

*Primary Examiner* — Mirellys Jagan
(74) *Attorney, Agent, or Firm* — thyssenkrupp North America, Inc.

(57) ABSTRACT

An apparatus for producing and analyzing sample materials may comprise a milling device for milling material components, a first metering device for metering a material component into the milling device, a second metering device for metering an activator liquid into the milled material component, a homogenization device for homogenizing the material components and the activator liquid to produce a sample material, a control device that is connected to the milling device and is configured to vary a parameter characteristic for milling intensity of the milling device so that particle size of the material components is altered, and a measuring device for determining a reactivity of the sample material. The present disclosure further concerns a process for producing and analyzing a plurality of sample materials. The process may involve varying at least one parameter characteristic for milling intensity for each sample material produced.

14 Claims, 2 Drawing Sheets

(51) Int. Cl.

| | |
|---|---|
| *G01K 13/00* | (2006.01) |
| *G01N 25/48* | (2006.01) |
| *C04B 7/52* | (2006.01) |
| *C04B 40/00* | (2006.01) |
| *G01N 33/38* | (2006.01) |
| *C04B 7/02* | (2006.01) |
| *C04B 7/32* | (2006.01) |
| *C04B 12/00* | (2006.01) |
| *B02C 21/00* | (2006.01) |
| *B02C 25/00* | (2006.01) |
| *C04B 7/345* | (2006.01) |
| *G01N 11/00* | (2006.01) |
| *G01N 15/02* | (2006.01) |

(52) U.S. Cl.
CPC ............... *C04B 7/02* (2013.01); *C04B 7/323* (2013.01); *C04B 7/345* (2013.01); *C04B 7/52* (2013.01); *C04B 12/005* (2013.01); *C04B 40/0032* (2013.01); *C04B 40/0082* (2013.01); *G01N 11/00* (2013.01); *G01N 15/02* (2013.01); *G01N 33/383* (2013.01); *Y02P 40/165* (2015.11)

(56) References Cited

OTHER PUBLICATIONS

Kumar, S. et al: "Mechanical activation of fly ash: Effect on reaction, structure and properties of resulting geopolymer", Ceramics International, Elsevier, Amsterdam, NL, vol. 37, No. 2, Mar. 1, 2011 (Mar. 1, 2011.

Liu, C. et al: "Effects of the granularity of raw materials on the hydration and hardening process of calcium phosphate cement", Biomaterials, Elsevier Science Publishers BV., Barking, GB, vol. 24, No. 23, Oct. 1, 2003 (Oct. 1, 2003).

Bohner, M. et al: "Combining particle size distribution and isothermal calorimetry data to determine the reaction kinetics of alpha-tricalcium phosphate-water mixtures", ACTA Biomaterialia, Elsevier, Amsterdam, NL, vol. 2, No. 3, May 1, 2006 (May 1, 2006).

E. Ferna'ndez et al: "Production and characterization of new calcium phosphate bone cements in the CaHPO 4 a-Ca 3 (PO 4) 2 system: pH, workability and setting times", Journal of Materials Science: Materials in Medicine, vol. 10, No. 4, Jan. 1, 1999 (Jan. 1, 1999).

Medina, C. et al: "Rheological and calorimetric behaviour of cements blended with containing ceramic sanitary ware and construction/demolition waste", Construction and Building Materials, Elsevier, Netherlands, vol. 40, Dec. 28, 2012 (Dec. 28, 2012).

English abstract of DE19634533C.

APPARATUS AND METHOD FOR PRODUCING AND ANALYZING A PLURALITY OF SAMPLE MATERIALS

CROSS REFERENCE TO RELATED APPLICATIONS

This application is a U.S. National Stage Entry of International Patent Application Serial Number PCT/EP2015/079880, filed Dec. 15, 2015, which claims priority to German Patent Application No. DE 10 2014 018 489.7 filed Dec. 16, 2014, the entire contents of both of which are incorporated herein by reference.

FIELD

The present disclosure generally relates to apparatuses and processes for producing and analyzing sample materials, including samples of a hydraulic binder.

BACKGROUND

Inorganic binders are used in an amount of about 4 Gt per annum in the building industry. The composition of the binders has altered in recent decades. Traditional cements based on portland cement clinker and sulfate carriers have frequently been replaced by sustainable, inexpensively producible composite cements which are composed of clinker, additives and sulfate carriers and have been optimized in respect of the use properties.

As a result of the increasing complexity of the binder composition, the required matching of the binder fineness and the use properties, the financial outlay and the time outlay in product optimization and product development have increased. The target parameters in product optimization and product development encompass, for example, the processability, the setting behavior and the development of strength. Finally, the performance of the binder in the main application of concrete has to be examined.

The high materials requirement for examination of concrete necessitates early preselection of suitable binder compositions and suitable binder fineness ranges. The usual physical analytical methods which are employed in the building industry and are described in EN 196 and EN 206 allow analysis of only a small number of samples because of the considerable materials requirement and are also very time-consuming to carry out because of, for example, the test age up to 28 days. Determination of the effect of the many different parameter variations on the reactivity of the binder is therefore very time-consuming.

DETAILED DESCRIPTION

Figure 1:
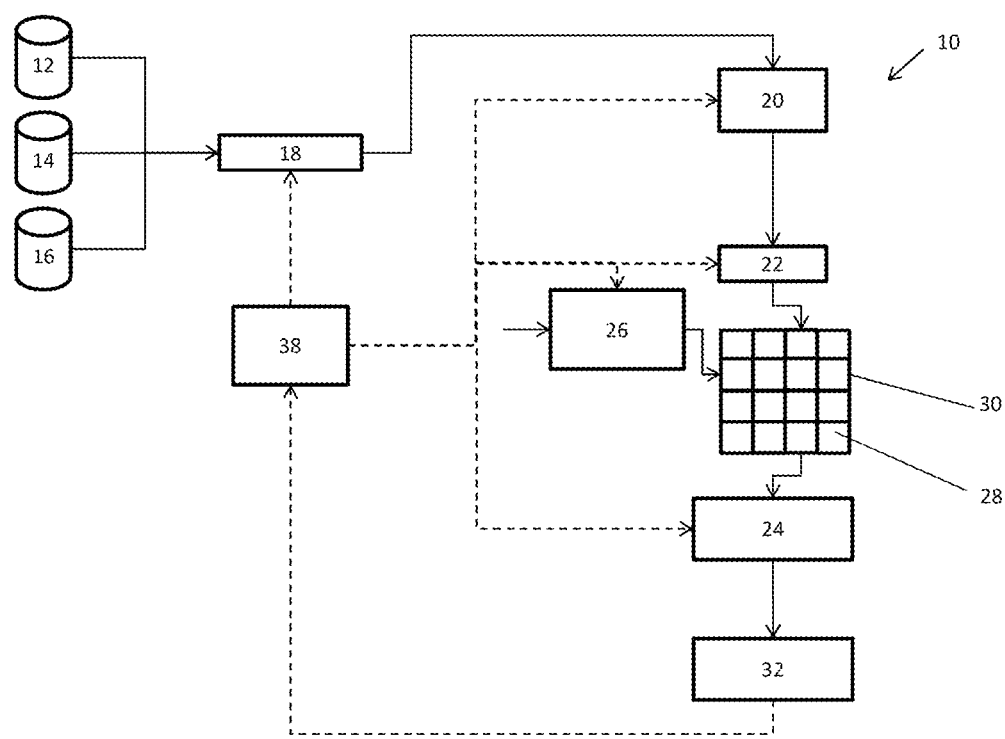
FIG. 1 is a schematic view of an example apparatus for analyzing a sample material.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting 'a' element or 'an' element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

Proceeding therefrom, it is an object of the present invention to provide an apparatus and also a process for producing and analyzing a plurality of sample materials in particular samples of a hydraulic binder, with analysis of the effect of a variation of different parameters on the reactivity of the binder in a simple and quick manner being made possible.

An apparatus for producing and analyzing a plurality of sample materials comprises, according to a first aspect, a milling device for milling material components, at least one first metering device for metering at least one material component into the milling device, at least one second metering device for metering an activator liquid into the at least one milled material component, a homogenization device for homogenizing the material components and the activator liquid to give a sample material. The apparatus additionally has a control device which is connected at least to the milling device and is configured in such a way that it varies at least one parameter characteristic for the milling intensity of the milling device so that, in particular, the particle size of the material components is altered. Furthermore, the apparatus has at least one measuring device for determining the reactivity of the sample material.

The milling device preferably comprises a fine mill, in particular an oscillatory disk mill which can be regulated in respect of the speed of rotation and the milling time. For example, the fine mill is automatically operated and comprises an automatic cleaning device. The milling device also encompasses, for example, a vibratory mill, a ball mill, a vertical roller mill or a high-compression roller mill.

For the purposes of the present invention, sample materials are, for example, hydraulic binders which have different compositions of various material components, for example clinker, sulfate carriers or additives. Additives are, for example, slag sand, fly ash, pozzolan, limestone or calcined clay.

A metering device for metering at least one material component into the milling device preferably comprises a weighing cell which automatically feeds, for example gravimetrically or volumetrically, a particular amount of a material component into the milling device. The metering device is connected directly or indirectly via an intermediate store with the milling device. For example, a metering device is provided for each material component or at least one milling device for metering a plurality of material components into the milling device is provided. For example, the metering device is integrated into the sample input region of the milling device.

A metering device for metering an activator liquid into the at least one milled material component comprises, for example, a regulable pump, for example in the form of a peristaltic pump or pipette. The activator liquid is, for example, water or an alkali solution.

A homogenization device for homogenizing the material components and the activator liquid to give a sample material preferably comprises a vibration device or a stirring device, with homogenization being carried out by means of vibration or stirring.

The control device is, for example, configured so that it varies the parameters characteristic for the milling intensity either electrically or mechanically. For example, the desired parameter value is entered manually on the control device or is determined by the control device from further parameters such as metered amount or particle size of the material components or the material composition.

A parameter characteristic for the milling intensity of the milling device is, for example, the speed of rotation, the gap width or the duration of milling of the material components. The milling intensity influences the particle size of the material components milled by means of the milling device, with a high milling intensity producing a small particle size and a low milling intensity producing a high particle size of the milled material components. Variation of the milling intensity therefore also varies the particle size of the material components.

To produce a sample material, a particular composition of the sample material or of a number of sample materials is preferably set via the control device, with the proportions of particular material components being, for example, able to be set manually on the control device or being able to be determined by the control device. The metering device meters a predetermined amount of material components into the milling device in which the material components are, for example, milled individually or together. The milled sample material is preferably introduced into a preferably liquid-impermeable sample container which is subsequently fed to the homogenization device. After the activator liquid has been metered into the milled material components in the sample container, the homogenized sample material is fed to the measuring device in order to determine the reactivity.

A control device which is configured in such a way that it varies at least one parameter characteristic for the milling intensity of the milling device makes it possible to produce a plurality of sample materials whose particle size varies in a known way. A large number of sample materials of differing fineness can be produced and analyzed in the measuring device in a simple manner. This makes it possible to determine the reactivity of the sample materials as a function of the particle size of the sample material in a simple manner, giving a high data density, based on the variation of the particle size. A precise analysis, in particular of nonlinear relationships between the reactivity and the particle size of the sample material, can be carried out, so that reliable optimization of these parameters is made possible.

In a first embodiment, the measuring device is a calorimetric measuring device, in particular an isothermal heat flow calorimeter. A calorimetric measuring device determines the heat of reaction given off by the sample material. The heat of reaction liberated and the course of the release of heat over time are characteristic for the reactivity of a sample material, in particular of a binder. The calorimetric measuring device allows simple and quick determination of the reactivity of the sample material.

In a further embodiment, the control device is connected to the metering device and is configured in such a way that it controls the metered amount of the material component. This allows variation of the amount of material components and of the particle size of the sample material by means of the control device, so that many sample materials having parameters which have been varied in a known way, e.g. particle size and composition of the sample material, can be produced and analysis of the reactivity as a function of the composition of the sample material is thus made possible.

At least one metering device is heatable in a further embodiment. This allows metered addition of a sulfate carrier with simultaneous thermal dewatering and thus targeted setting and utilization of partial or complete sulfate carriers in the sample materials.

The apparatus additionally has a crushing device which is installed upstream of the milling device. The crushing device allows precomminution of material components which comprise, for example, granules having a size of about 3-10 mm. A crushing device also increases the metering accuracy of material components having a large particle size.

In a further embodiment, the apparatus has a rheometric measuring device for determining the rheological properties of the sample material. Rheometric measurement methods allow simple determination of the dependence of the rheometric properties of the sample material on parameters such as particle size and composition of the sample material.

The apparatus has, in a further embodiment, a sample store having a plurality of sample containers for accommodating a sample material. Such a sample store allows simultaneous analysis of a plurality of sample containers containing sample materials in a measuring device such as a calorimetric or rheological measuring device. This shortens the time for analysis of a plurality of sample materials considerably.

The measuring device is, in a further embodiment, configured in such a way that it simultaneously determines the reactivity of a plurality of sample materials.

In a further embodiment, the apparatus additionally comprises a metering device for metering at least one cement additive into the at least one milled material component located downstream of the milling device. The control device is preferably connected to the metering device so that the amount of cement additives can be set via the control device. Cement additives are, for example, milling aids such as DEG (diethylene glycol) or TEA (triethanolamine) or organic or inorganic additives which modify the cement properties (e.g. TIPA, $CaCl_2$).

The control device is preferably connected to the metering device for metering the activator liquid so that the amount of activator liquid can be controlled via the control device and the reactivity of the sample material as a function of the amount of activator liquid can be determined. Metering is effected, for example, via a peristaltic pump or a pipette.

The apparatus is preferably located in a temperature-regulated isothermal environment, for example a laboratory room. This makes it possible, for example when the measuring device comprises an isothermal heat flow calorimeter, to decrease the load on the thermostat of the measuring device, with the temperature required for optimal measurement being set in the total apparatus.

A process for producing and analyzing a plurality of sample materials, in particular samples of a hydraulic binder, has the following steps:

a) metering at least one material component into a milling device
b) milling the at least one material component in the milling device
c) metering an activator liquid into the at least one material component
d) homogenizing the at least one material component and the activator liquid to give a sample material, wherein the steps a) to d) are repeated to produce a plurality of sample materials, with at least one parameter characteristic for the milling intensity being varied on the milling plant and the process additionally having the step of determining the reactivity of the plurality of sample materials by means of a calorimetric measuring device.

The advantages described above for the apparatus apply analogously to the process for producing and analyzing a plurality of sample materials.

In a first embodiment, the speed of rotation of the milling device and/or the milling time of the at least one material component is varied in step b).

Furthermore, in a further embodiment, the rheological properties of the plurality of sample materials are determined.

The at least one material component is, in a further embodiment, crushed before step b).

In a further embodiment, step a) comprises heating at least one material component.

The particle size of at least part of the milled material components is, in a further embodiment, determined before step d). Determination of the fineness or particle size distribution of the sample, for example by means of sieving or a laser granulometer, allows correlation of the measurement results with a particle size parameter and easy transfer of the newly developed material into industrial production.

FIG. 1 schematically shows an apparatus 10 for analyzing a sample material. The analysis apparatus 10 has, by way of example, three containers 12, 14 and 16 in each of which a material component is stored. The depiction of three containers 12, 14, 16 is merely by way of example; it is conceivable to provide many containers each containing a material component in the analysis apparatus 10.

The material components are in particular material components of a binder such as cement. For example, clinker such as portland cement clinker or sulfoaluminate clinker together with a sulfate carrier and additives are used for producing binders. A sulfate carrier is, for example, gypsum, hemihydrate, anhydrite or other materials having an elevated $SO_3$ content. Additives are, for example, latently hydraulic materials, slag sand, brown coal fly ash, silica dust or pozzolans such as hard coal fly ash, natural pozzolans, synthetic pozzolans or filler materials such as limestone. The material components are stored in the containers 12, 14, 16, preferably as crushed material having a particle size of up to 3 mm, as powder having a particle size of up to about 0.09 mm or as granules having a particle size of from about 3 to 10 mm.

The analysis apparatus 10 additionally has a first metering device 18 which is connected to the containers 12, 14 and 16. The metering device 18 is, for example, a weighing cell, a balance or a volumetric measuring device. The metering device conveys a particular amount of the material components out of the respective container 12, 14, 16. The metering accuracy of the metering device is, based on the total amount weighed out, about 0.01-1%, preferably 0.007%-0.25%, most highly preferably about 0.5%.

A milling device 20 is installed downstream of the metering device 18. The milling device 20 is, for example, an oscillatory disk mill or a vibratory mill. The metering device 18 meters a particular amount of a material component from one of the containers 12, 14 and 16 into the milling device 20. The material components are, for example, conveyed directly from one of the containers 12, 14, 16 via the metering device 18 to the milling device 20 or combined in an intermediate store (not shown) and subsequently fed together to the milling device 20.

The milling device 20 is followed by a further optional metering apparatus 22 and a homogenization device 24, a second metering device 26 for metering an activator liquid and a sample store 30 having a plurality of sample containers 28.

The analysis apparatus 10 additionally has a calorimetric measuring device 32 for determining the reactivity of a sample material and also a rheometric measuring device 34 for determining the processing properties of the sample material.

Furthermore, the analysis apparatus 10 has a control device 38 which is connected to the first metering device 18, the milling device 20, the activator liquid metering device 26, the homogenization device 24 and the measuring devices 32 and 34.

In an analysis method by means of the analysis device 10, a particular composition of the sample material can be set via the control device 38. The proportions of the material components from the containers 12, 14, 16 in the sample material can, for example, be set manually on the control device 38 or can be calculated by the control device 38 at a predetermined interval, so that a plurality of sample materials having a proportion of a material component which varies over a particular quantity interval can be analyzed. The control device 38 is connected to the metering device 18 in such a way that the metered amount of material components set on the control device 38 is metered by means of the metering device 18 from the containers 12, 14, 16 into the milling device. The material components are subsequently milled individually or together in the milling device 20. In the case of joint milling of the material components, the material components are metered in succession into a sample container which is not shown in FIG. 1 and subsequently fed to the milling device.

The speed of rotation or the speed of vibration of the milling device 20 and also the duration of the milling process and thus the milling intensity can, for example, be set via the control device 38. A particular fineness of the sample material can thus be set on the milling device 20 via the control device 38.

After the milling device 20, the sample material is metered by means of a metering apparatus 22 into a sample container 28. The metering apparatus 22 determines, for example, the net weight of the sample material introduced into the sample container 28. For example, the metering device determines the net weight of the sample container 28, the total weight of the sample container 28 with the sample material and/or the net weight of the sample material introduced into the sample container 28.

The sample container is arranged in a sample store 30 which has a plurality of sample containers 28 which, for example, each contain different sample materials. In the working example depicted in FIG. 1, the sample store encompasses sixteen sample containers 28 which are arranged in four rows.

The above-described steps are preferably repeated with variation of the parameters which can be controlled by the control device 38, so that a plurality of different sample compositions are arranged in different sample containers 28 in the sample store 30.

An activator liquid is fed via the activator liquid metering device 26 into the sample container 28. If one of the material components is portland cement clinker or sulfoaluminate clinker, water is metered as activator liquid into the sample container 28. If one of the material components is a geopolymer, an alkali solution is metered as activator liquid into the sample container 28. The activator liquid metering device 26 has, for example, a heating device for heating the activator liquid, in particular to the temperature of the calorimetric measuring device 32. The metering accuracy of the metering device 26 is not more than about 0.001-1%, preferably 0.007-0.25%, most highly preferably about 0.5%, of the desired metered amount.

In particular, an activator liquid is metered via the activator liquid metering device 26 into the material components in the sample container 28 so that the ratio of liquid to sample material is about 0.25-1.2, in particular 0.4-0.6, particularly preferably 0.45-0.55. The activator liquid and the material components are homogenized in the sample container in the homogenization device 24 to give a sample material. The homogenization device 24 comprises, for example, a vibratory apparatus by means of which the sample container is subjected to vibration. The homogenization 24 can also be carried out by means of mechanical mixing such as stirring or knocking.

The sample container 28 in the sample store 30 is subsequently introduced into the calorimetric measuring device 32. It is likewise conceivable to introduce the sample container separately, without sample store 30, into the calorimetric measuring device 32.

The addition of the activator liquid to the material components starts the hydration process, with the energy stored in the material components being liberated in the form of heat of reaction. The sample container 28 is therefore introduced into the measuring device 32 immediately after addition of the activator liquid and the subsequent homogenization, so that the entire heat of reaction liberated is preferably measurable. For example, the heat of reaction is energy in the clinker stored beforehand in the mineral phases by cooling in a clinker cooler. This heat of reaction is characteristic of the reactivity of the mixture of the material components. The cumulative energy liberated to any point of time during hydration corresponds to the weighted average of the contribution of the individual material components. The degree of hydration and the hydration rate is determined by the mineralogical composition of the material components, in particular the clinker, the sulfate carrier added and the surface area produced during milling of the material components. The hydration reaction proceeds isochemically, with the freshly formed hydrate phases being largely X-ray amorphous.

The calorimetric measuring device 32 is configured in such a way that it determines the heat given off by the sample material over a particular period of time.

Commercially available calorimeters, for example isothermal heat flow calorimeters, make it possible to determine the heat of hydration of a plurality of different sample materials in parallel over a particular time. Known calorimeters have a plurality of measuring channels in which different sample materials are analyzed at the same time. The calorimetric measuring device 32 is configured in such a way that small sample quantities, for example 1-10 g, preferably 3-8 g, very highly preferably about 5 g, are sufficient for determining the reactivity of the sample material. The measuring device 32 determines the heat of hydration over, for example, a measurement time of about 1-8 days, in particular 4-6 days, preferably 5 days, at a temperature in the calorimeter of about 20-45° C., in particular 20-27° C. Raising the temperature to about 45° C. makes a short measurement time of less than one day also conceivable.

The calorimetric measuring device 32 transmits the measurement result to the control device 38. The control device 38 is, furthermore, configured in such a way that it determines a reactivity of the sample material by means of the heat given off by the sample material, as determined by the calorimetric measuring device.

Figure 2:
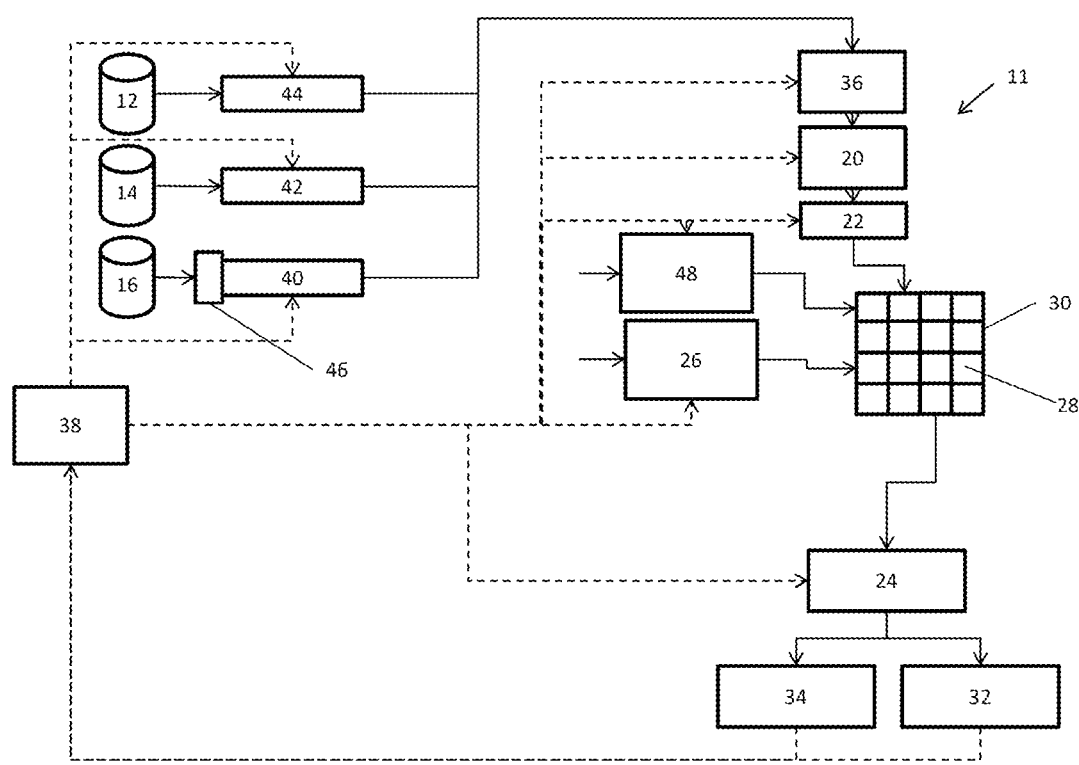
FIG. 2 is a schematic view of another example apparatus for analyzing another sample material.

Between the elements of the analysis apparatus 10, there are, for example, transport devices such as conveyor belts, mobile robots or fixed-position robots having a long reach which are shown schematically as arrows in FIGS. 1 and 2.

FIG. 2 schematically shows an apparatus 11 for analyzing a sample material as per a further working example. The analysis apparatus 11 has all elements of the analysis apparatus 10 described with reference to FIG. 1, with the metering device 18 of the analysis device 10 having been replaced by three metering devices 40, 42, 44 and the metering device 40 additionally having a heating device 46. Furthermore, the analysis device 11 of FIG. 2 has a further crushing device 36 located upstream of the milling device 20 and also a third further metering device 48 for metering solid or liquid additives, for example milling aids (e.g. DEG, TEA) or cement additives (e.g. TIPA, $CaCl_2$) into the sample container 28.

The analysis apparatus 11 also has a rheometric measuring device 34 for determining the rheological properties of the sample materials in the sample containers 28 of the sample store 30.

The analytical method which can be carried out by means of the analysis apparatus 11 corresponds substantially to the analytical method described with reference to FIG. 1, with each of the containers 12, 14, 16 being assigned a metering device 40, 42, 44 which meters an amount of material components which can be set by means of the control device 38 into the crushing device 36. The metering device 40 which is assigned to the container 16 has a heating device 46 by means of which the material component from the container 16 is heatable. The material component in the container 16 is, for example, a sulfate carrier which is heated and thus thermally dewatered by means of the heating device 46.

The crushing device 36 breaks, in particular, material components having a large particle size, e.g. granules having a particle size of from about 3 to 10 mm, before introduction of the material components into the milling device 20.

Furthermore, the analytical method by means of the analysis apparatus 11 comprises a rheometric measurement by means of the rheometric measuring device 34. The rheometric measuring device 34 determines the rheological properties, for example the flow limit, of at least part of the sample material in the sample containers 28 of the sample store 30.

In the analysis apparatuses 10 and 11, parameters such as the proportions by mass of the material components from the containers 12, 14, 16 in the sample material, the degree of milling of the material components and the amount of activator liquid and additives of the sample material can be set by means of the control device, so that it is possible to produce many sample materials for which one or more parameters vary in a known manner. Analysis of the plurality of sample materials in a sample store 30 at the same time in the calorimetric measuring device 32 makes it possible to determine the reactivity of a material as a function of particular parameters such as particle size and composition of the material in a simple manner. Furthermore, the analysis device 10, 11 makes it possible to produce a large number of sample materials in a simple manner and thus produce a high data density based on the variation of the parameters. This makes precise analysis, in particular of nonlinear relationships between the reactivity or the rheological properties and the parameters of the sample materials, e.g. composition and particle size, possible.

LIST OF REFERENCE NUMERALS

10 Analysis apparatus
11 Analysis apparatus
12 Store
14 Store
16 Store
18 First metering device
20 Milling device
22 Metering device
24 Homogenization device
26 Second metering device for metering an activator liquid
28 Sample container
30 Sample store
32 Measuring device
34 Measuring device
36 Crushing device
38 Control device
40 Metering device
42 Metering device
44 Metering device
46 Heating device
48 Third metering device

What is claimed is:

1. An apparatus for producing and analyzing sample materials, the apparatus comprising:
    a milling device configured to mill material components;
    a first metering device configured to meter a plurality of material components into the milling device;
    a second metering device configured to meter an activator liquid into the plurality of material components that have been milled in the milling device;
    a homogenization device configured to homogenize the plurality of material components and the activator liquid to produce a sample material;
    a control device that is connected to the milling device and is configured to vary a parameter characteristic for a milling intensity of the milling device so as to alter particle size of the plurality of material components; and
    a measuring device configured to determine a reactivity of the sample material, wherein the control device is connected to the first metering device and is configured to control a metered amount of the plurality of material components.

2. The apparatus of claim 1, wherein the measuring device is a calorimetric measuring device.

3. The apparatus of claim 1, wherein the first metering device is configured to be heated.

4. The apparatus of claim 1, further comprising a crushing device disposed upstream of the milling device.

5. The apparatus of claim 1, further comprising a rheometric measuring device configured to determine rheological properties of the sample material.

6. The apparatus of claim 1, further comprising a third metering device configured to meter a cement additive into the plurality of material components downstream of the milling device.

7. The apparatus of claim 1, further comprising a sample store with a plurality of sample containers for accommodating a plurality of sample materials.

8. The apparatus of claim 7, wherein the measuring device is configured to simultaneously determine reactivities of the plurality of sample materials.

9. A process for producing and analyzing a plurality of sample materials, the process comprising:
    metering a plurality of material components into a milling device;
    milling the plurality of material components in the milling device;
    metering an activator liquid into the plurality of material components;
    homogenizing the plurality of material components and the activator liquid to produce a sample material;
    repeating the above steps to produce a plurality of sample materials, wherein a parameter characteristic for a milling intensity is varied for each of the plurality of sample materials produced; and
    determining a reactivity of each of the plurality of sample materials with a calorimetric measuring device.

10. The process of claim 9, wherein at least one of a speed of rotation of the milling device or a milling time of the plurality of material components is varied during the milling of the plurality of material components in the milling device.

11. The process of claim 9, further comprising determining rheological properties of the plurality of sample materials.

12. The process of claim 9, further comprising crushing the plurality of material components prior to milling the plurality of material components in the milling device.

13. The process of claim 9, wherein the metering of the plurality of material components into the milling device comprises heating the plurality of material components.

14. The process of claim 9, further comprising determining particle size of at least part of the milled plurality of material components prior to homogenizing the plurality of material components.

* * * * *